United States Patent [19]

Kacher et al.

[11] Patent Number: 5,312,559

[45] Date of Patent: * May 17, 1994

[54] PERSONAL CLEANSER WITH MOISTURIZER

[75] Inventors: Mark L. Kacher, Mason; Julie A. Wagner, Cincinnati; James R. Schwartz, West Chester; Efrain Torres; Marcus W. Evans, both of Cincinnati; James E. Taneri, West Chester, all of Ohio

[73] Assignee: The Procter & Gamble Company, Cincinnati, Ohio

[ * ] Notice: The portion of the term of this patent subsequent to May 3, 2011 has been disclaimed.

[21] Appl. No.: 909,877

[22] Filed: Jul. 7, 1992

[51] Int. Cl.$^5$ .................. C11D 9/24; C11D 9/48; C11D 17/00; C11D 17/02
[52] U.S. Cl. .................. 252/125; 252/126; 252/127; 252/130; 252/132; 252/134; 252/173; 252/174.18; 252/174.23; 252/368; 252/546; 252/DIG. 5; 252/DIG. 14; 252/DIG. 16
[58] Field of Search ............... 252/125, 122, 123, 132, 252/134, 126, 174.17, 174.23, 367, 368, 174.18, 546, 127, 130, 173, DIG. 2, DIG. 5, DIG. 16; 514/762, 846, 847, 873; 424/78.03, 489, 502

[56] References Cited

U.S. PATENT DOCUMENTS

| | | | |
|---|---|---|---|
| 3,829,563 | 8/1974 | Barry et al. | 424/70 |
| 4,673,525 | 6/1987 | Small et al. | 252/122 |
| 4,820,447 | 4/1989 | Medcalf, Jr. et al. | 252/174.17 |
| 4,821,253 | 3/1989 | Small et al. | 252/122 |
| 5,002,680 | 3/1991 | Schmidt et al. | 252/132 |
| 5,076,953 | 12/1991 | Jordan et al. | 252/122 |
| 5,096,608 | 3/1992 | Small et al. | 252/122 |
| 5,147,574 | 9/1992 | MacGilp et al. | 252/108 |
| 5,158,699 | 10/1992 | MacGilp et al. | 252/132 |

*Primary Examiner*—Linda Skaling
*Assistant Examiner*—A. Hertzog
*Attorney, Agent, or Firm*—Leonard Williamson

[57] ABSTRACT

A very stable mild soap personal cleansing and moisturizing composition comprising: $C_8$–$C_{22}$ free fatty acid soap, $C_8$–$C_{22}$ free fatty acid, water, and petrolatum, or emollient preferably having a weight average particle size larger than 45 microns.

34 Claims, No Drawings

PERSONAL CLEANSER WITH MOISTURIZER

TECHNICAL FIELD

The present invention is related to personal cleansing products, especially cleansers and creams for bath or shower which are formulated for mildness, viscosity control, phase stability, and moisturization.

BACKGROUND OF THE INVENTION

Personal cleansing compositions are well known.

The need for mild skin cleansing compositions is made more acute by both the aging of the human population and the ever-increasing environmental insult to which the skin is subject. The mildest skin cleansing products can, at best, produce cleansing without negatively affecting the skin condition. To achieve an improvement in skin condition, the consumer is forced to use a second, separate product often called a "moisturizer". The use of two separate products to achieve the desired skin state is inconvenient and often unpleasant due to the greasy skin feel resultant from many moisturizers. As a result, many persons suffer from the effects of poor skin condition rather than use two separate products.

There is a clear need for a single product which is capable of delivering both mild skin cleansing and a skin conditioning benefit. Many skin cleansing products contain humectant substances which, although effective in topical application, are ineffective in cleansing products. These humectants are ineffective because they are very water soluble and suffer from poor skin substantivity. Hydrophobic emollient materials are generally more substantive to the skin, but are more difficult to incorporate into an aqueous skin cleansing matrix. There are at least two sources of difficulty typically encountered: poor lather effects and physically unstable product.

U.S. Pat. No. 3,829,563, Barry et al., issued Aug. 13, 1974, discloses a liquid skin cleansing composition containing petrolatum in the range of 10–70% having a diameter particle size of (>95%) smaller than 5 microns.

U.S. Pat. No. 4,673,525, Small et al., issued Jun. 16, 1987, incorporated herein by reference, discloses mild surfactant based personal cleansing systems, primarily synbars.

Most non-solid soaps comprise mostly "soluble," "unsaturated," or shorter chains, e.g., lauric/oleic soaps for phase stability. This, however, compromises lather quality and/or mildness.

The present invention allows for the incorporation of substantially larger petrolatum particles than the prior art. These larger particles result in greater functional efficacy than previously has been achieved.

OBJECT OF THE INVENTION

One object of this invention is to provide a personal cleansing product which conditions and moisturizes the skin as the product is used. Another object of this invention is to provide a single product which achieves the benefits of using two separate products for cleansing and moisturizing the skin.

A further object is to provide processes for making these products.

It is still another object of the present invention to provide a semi-solid cleansing bath/shower soap composition which is phase stable, shelf stable, lathers well, and is cosmetically attractive.

It is a further object of the present invention to provide a semi solid soap cleansing composition which is relatively mild.

These and other objects of the present invention will become obvious from the detailed description which follows.

SUMMARY OF THE INVENTION

The present invention relates to a stable dispersoidal semi-solid personal cleansing composition comprising:

(A) from about 7% to about 33% by weight of potassium $C_8$–$C_{22}$ fatty acid soap;

(B) from about 4% to about 18% $C_8$–$C_{22}$ free fatty acid;

(C) from about 40% to about 70% water; and (D) from about 5% to about 30% of a polyol selected from the group consisting of: glycerin (glycerol), propylene glycol, polypropylene glycols, polyethylene glycols, ethyl hexanediol, hexylene glycols, and other aliphatic alcohols; and mixtures thereof; and (E) from about 0.5% to about 15% petrolatum emollient, preferably having a weight average particle size of from about 45 microns to about 120 microns.

DETAILED DESCRIPTION OF THE INVENTION

The present invention relates to a stable dispersoidal semi-solid soap cleansing composition comprising: 40% to 70%, preferably 45% to 65%, water; 7% to 33%, preferably 9% to 25%, of mostly insoluble saturated (low IV Iodine Value) higher fatty acid potassium soap; 4% to 18%, preferably 5% to 17%, of free fatty acids; and 0.5% to 15%, preferably 0.7% to about 13% petrolatum. The soap and the free fatty acids have a preferred ratio of above about 1.3:1 to about 1.8:1 and more preferably from about 1.35:1 to about 1.75:1. The semi-solid compositions having petrolatum at levels of from 0.5% to 6% preferably have a weight particle size of from 45 micron to 120 micron, but have improved mildness over comparable compositions without petrolatum notwithstanding the particle size of the petrolatum.

This invention relates to a semi-solid composition and also a bar composition suitable for cleansing and "conditioning" or "moisturization" of the skin. The "conditioning" benefit is defined as the deposition of a material on the skin surface which is known to improve skin condition and at a level that surpasses the threshold for a noticeable benefit.

The present invention is concerned with the ability to incorporate petrolatum and/or an equivalent into an aqueous skin cleansing matrix and maintain the larger particle size that results in functional efficacy without producing an unstable product. Formulations and processes have been invented which allow the petrolatum particle size to be increased to a weight average particle size of from about 45 microns to about 120 microns within the product, preferably from about 50–110 microns, more preferably from about 55–110 microns. It will be demonstrated that the larger particles result in improved skin deposition.

A very stable mild dispersoidal semi-solid soap personal cleansing composition comprising:

(A) from about 7% to about 33% by weight of potassium $C_8$–$C_{22}$ fatty acid soap;

(B) from about 4% to about 18% $C_8$–$C_{22}$ free fatty acid;
(C) from about 40% to about 70% water (preferably $C_{10}$–$C_{20}$); and
(D) from about 5% to about 30% of a polyol selected from the group consisting of: glycerin (glycerol), propylene glycol, polypropylene glycols, polyethylene glycols, ethyl hexanediol, hexylene glycols, and other aliphatic alcohols; and mixtures thereof; and
(E) from about 0.5% to about 15%, preferably 1–6%, petrolatum having a weight average particle size larger than 45 microns;

wherein said fatty acid of said (A) and (B) has an Iodine Value of from zero to about 15; wherein said soap and said free fatty acid have a weight ratio of about 1.3:1 to about 1.8:1; and wherein said semi-solid has a viscosity of from about 60,000 cps to about 400,000 cps at 25° C.

An improved stable product with improved moisturizing benefit is achieved with the incorporation of larger sized petrolatum particles into selected fatty acid and/or soap matrixes. The larger sized petrolatum particles will vary for a liquid, semisolid, or bar. The key is to select the fatty acid and/or soap matrix as exemplified herein, and mix in the petrolatum using a minimal controlled amount of shear to maintain larger petrolatum particles and achieve a homogeneous stable product, e.g., an improved stable liquid personal cleanser with improved moisturizing benefits is disclosed in commonly assigned U.S. patent application Ser. No. 07/909,834 filed of even date, Dias et al.

Petrolatum and Other Emollients

A requirement for the present compositions is that they contain from about 0.5% to about 15% petrolatum, having a weight average particle size larger than about 45 microns.

The petrolatum useful in the present invention can be any grade of white or yellow petrolatum recognized in the art as suitable for human application. The preferred type is USP Class III with a melting point between 122° and 135° F. (50° and 57° C.). Such a material is commercially available as Penreco Snow White Pet USP. The petrolatum of the present invention includes hydrocarbon mixtures formulated with mineral oils in combination with paraffin waxes of various melting points.

Alternatively, the composition of the present invention can contain from about 0.5% to about 15% of a lipophilic emollient selected from the group consisting of: petrolatum; esters of fatty acids wherein said fatty acids are of structure

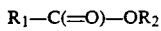

and wherein
$R_1, R_2 = C_8$–$C_{22}$, ricinoleate, 12-hydroxy stearic and wherein $R_1$ and/or $R_2$ alkyl chain can be saturated or unsaturated; glycerin mono-, di-, and tri-esters; epidermal and sebaceous hydrocarbons such as cholesterol, cholesterol esters, squalene, squalane; silicone oils and gums; mineral oil; lanolin and derivatives and the like; and mixtures thereof. The petrolatum and/or emollient particle size is alternatively expressed as a particle size distribution with 10% to 80% of the particles being about 5 microns to about 120 microns within the product, preferably 20% to 80% being from about 10–110 microns, more preferably 25% to 80% from about 30–110 microns, more preferably 60–100 microns.

Personal Cleansing Solid Bar

The present invention includes a solid bar composition. Specifically, a stable personal cleansing solid bar composition, by weight, comprises:
(A) from about 5% to about 75% of a substantially saturated fatty acid material selected from the group consisting of: $C_8$–$C_{22}$ free fatty acid and fatty soap and mixtures thereof;
(B) from about 10% to about 90% water; and
(C) from about 0.5% to about 35% petrolatum having a particle size of distribution with from 10%–80% being from 5 microns to about 120 microns.

Methods of Making Semi-Solid and Bar

The semi-solid composition is preferably made by (1) heating and mixing free fatty acid to provide a stable melt; (2) forming soap in situ by adding aqueous potassium hydroxide to provide a dispersion of soap and free fatty acid having said ratio of about 1.3:1 to about 1.8:1; and (3) adding water, polyol and mild, lathering surfactant to said dispersion with mixing; (4) cooling the dispersion of Step 3 to a temperature below the melting point of petrolatum; and (5) adding said petrolatum with mixing to provide said dispersoidal semi-solid personal cleansing composition.

The solid bar is made by: (1) heating and mixing free fatty acid to provide a stable melt; (2) forming soap in situ by aqueous sodium hydroxide, sodium chloride, and water to provide a heated mix; (3) adding other ingredients such as polyols, synthetic surfactants, etc., to said heated mix; (4) adding petrolatum to the said heated mix (3) using low shear and minimal mixing time to provide a homogeneous mix; (5) pouring the heated homogeneous mix of (4) into bar molds and cooling to provide solid personal cleansing bars.

The Fatty Acid

The fatty acid matter of the present invention has an IV of from zero to about 15, preferably below 10, more preferably below 3.

The compositions contain fatty acids derived from essentially saturated hydrocarbon chainlengths of from about 10 to about 22. These fatty acids may be highly purified individual chainlengths and/or crude mixtures such as those derived from fats and oils. In general, the higher the proposition of longer chainlength fatty acids, the poorer the lather, but the greater the pearlescent appearance and mildness of the product.

The ratio of soap to fatty acid is an important determinant of overall product rheology. The higher the ratio of soap to fatty acid, the thinner the product is. For the semi-solid composition, the ratio of soap to fatty acid is from about 1.3:1 to 1.8:1, preferably from about 1.35:1 to 1.75:1. If the soap to fatty acid ratio is larger than the specified range, poor lather results, if it is lower than the specified range, poor product stability (oil syneresis) results.

The semi-solid soap cleanser has a viscosity of 60,000–400,000 cps, preferably 70,000 cps to about 200,000 cps at about 25° C., Brookfield RVTDV-II with a Spindle D or F at 5 rpm.

The Soap

The compositions contain soaps derived from the essentially saturated hydrocarbon chainlengths of from about 10 to about 22, It is preferred that the soap be the potassium salt, but other soluble soaps can be used. Some sodium, ammonium, triethanolammonium, and/or mixtures thereof, are deemed acceptable, at least in potassium blends. The soaps are preferably prepared in situ soap by neutralization of the corresponding fatty acids, but they may also be introduced as preformed soaps.

The semi-solid soap is called a dispersoid because at least some of the fatty matter at the levels used herein is insoluble. The level of water in the semi-solid compositions is typically from about 40% to about 70%, preferably from about 45% to about 65%.

Another important attribute of the preferred semi-solid soap of the present invention is it is phase stable, particularly after storage.

The Polyol

The present invention contains from about 5% to about 30% of a polyol selected from the group consisting of: glycerin (glycerol), propylene glycol, polypropylene glycols, polyethylene glycols, ethyl hexanediol, hexylene glycols, and other aliphatic alcohols; and mixtures thereof; and preferably contains 10-25% of said polyol, preferably the polyol is glycerol.

The term "viscosity" as used herein means both of these viscosities as measured by a Brookfield RVTDV-II/Spindle D or F at 5 rpm at 25° C., unless otherwise specified.

Optionals

If present, the optional components individually generally comprise from about 0.001% to about 10% by weight of the composition, but can be more or less.

Optional thickeners are categorized as cationic, nonionic, or anionic and are selected to provide the desired viscosities. Suitable thickeners are listed in the Glossary and Chapters 3, 4, 12 and 13 of the *Handbook of Water-Soluble Gums and Resins,* Robert L. Davidson, McGraw-Hill Book Co., New York, N.Y., 1980, incorporated by reference herein.

The liquid personal cleansing products can be thickened by using polymeric additives that hydrate, swell or molecularly associate to provide body (e.g., hydroxypropyl guar gum is used as a thickening aid in shampoo compositions).

The nonionic cellulosic thickeners include, but are not limited to, the following polymers:
1. hydroxyethyl cellulose;
2. hydroxymethyl cellulose;
3. hydroxypropyl cellulose; and
4. hydroxybutyl methyl cellulose.

The anionic cellulosic thickener includes carboxymethyl cellulose and the like.

Another thickener is xanthan gum having a molecular weight (M.W.) of from about 2,000,000±500,000. Each molecule has about 2,000 repeating units.

Another thickener is acrylated steareth-20 methylacrylate copolymer sold as Acrysol ICS-1 by Rohm and Haas Company.

Another thickener is Natrosol ® 250 KR, sold by the Aqualon Co.

The amount of polymeric thickener found useful in the present compositions is about 0.1% to about 2%, preferably from about 0.2% to about 1.0%.

The semi-solid soap of the present invention can be made with from about 0.1% to about 5%, preferably from about 0.3% to about 3%, of a cationic polymer selected from the group consisting of: cationic polysaccharides and derivatives, cationic copolymers of saccharides and synthetic monomers, synthetic copolymers and cationic protein derivatives. Detailed lists of suitable cationic polymers are set out in Small et al. and Medcalf et al., incorporated herein by reference.

Another component useful in the present invention is a nonionic. The preferred nonionic is polyglycerol ester (PGE).

Groups of substances which are particularly suitable for use as nonionic surfactants are alkoxylated fatty alcohols or alkylphenols, preferably alkoxylated with ethylene oxide or mixtures of ethylene oxide or propylene oxide; polyglycol esters of fatty acids or fatty acid amides; ethylene oxide/propylene oxide block polymers; glycerol esters and polyglycerol esters; sorbitol and sorbitan esters; glycol esters and polyglycol esters; polyglycol esters of glycerol; ethoxylated lanolin derivatives; and alkanolamides and sucrose esters.

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethanolamide) pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate.

A preferred semi-solid composition also contains from about 0.5% to about 10% of an emollient selected from the group consisting of: esters of fatty acids; glycerin mono-, di-, and tri-esters; epidermal and sebaceous hydrocarbons such as cholesterol, cholesterol esters, squalene, squalane; lanolin and derivatives; silicone oils and gums, and the like.

The Surfactant

An important attribute of the preferred soap personal cleansing product of the present invention is its rich and creamy lather.

The preferred composition also contains from about 2% to about 8%, preferably from about 2.5 to about 6.5%, of a high lathering synthetic surfactant.

An important optional component of the present compositions is a lather boosting surfactant. The surfactant, which may be selected from any of a wide variety of anionic (nonsoap), amphoteric, zwitterionic, nonionic and, in certain instances, cationic surfactants, is present at a level of from about 1% to about 10%, preferably from about 2% to about 6% by weight of the product.

The cleansing product patent literature is full of synthetic surfactant disclosures. Some preferred surfactants as well as other cleansing product ingredients are disclosed in the following references:

| U.S. Pat. No. | Issue Date | Inventor(s) |
| --- | --- | --- |
| 4,061,602 | 12/1977 | Oberstar et al. |
| 4,234,464 | 11/1980 | Morshauser |
| 4,472,297 | 9/1984 | Bolich et al. |
| 4,491,539 | 1/1985 | Hoskins et al. |
| 4,540,507 | 9/1985 | Grollier |
| 4,565,647 | 1/1986 | Llenado |
| 4,673,525 | 6/1987 | Small et al. |

| U.S. Pat. No. | Issue Date | Inventor(s) |
|---|---|---|
| 4,704,224 | 11/1987 | Saud |
| 4,788,006 | 11/1988 | Bolich, Jr., et al. |
| 4,812,253 | 3/1989 | Small et al. |
| 4,820,447 | 4/1989 | Medcalf et al. |
| 4,906,459 | 3/1990 | Cobb et al. |
| 4,923,635 | 5/1990 | Simion et al. |
| 4,954,282 | 9/1990 | Rys et al. |

All of said patents are incorporated herein by reference. A preferred synthetic surfactant is shown the Examples herein. Preferred synthetic surfactant systems are selectively designed for appearance, stability, lather, cleansing and mildness.

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radiolabeled water ($^3H-H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, Small et al., issued Jun. 16, 1987, incorporated herein by reference, and which disclose a mild alkyl glyceryl ether sulfonate (AGS) surfactant based synbar comprising a "standard" alkyl glyceryl ether sulfonate mixture. Barrier destruction testing is used to select mild surfactants. Some preferred mild synthetic surfactants are disclosed in the above Small et al. patents and Rys et al.

Some examples of good lather-enhancing, mild detergent surfactants are e.g., sodium or potassium lauroyl sarcosinate, alkyl glyceryl ether sulfonate, sulfonated fatty esters, and sulfonated fatty acids.

Numerous examples of other surfactants are disclosed in the patents incorporated herein by reference. They include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates.

Alkyl chains for these surfactants are $C_8-C_{22}$, preferably $C_{10}-C_{18}$, more preferably $C_{12}-C_{14}$. Alkyl glycosides and methyl glucose esters are preferred mild nonionics which may be mixed with other mild anionic or amphoteric surfactants in the compositions of this invention. Alkyl polyglycoside detergents are useful lather enhancers. The alkyl group can vary from about 8 to about 22 and the glycoside units per molecule can vary from about 1.1 to about 5 to provide an appropriate balance between the hydrophilic and hydrophobic portions of the molecule. Combinations of $C_8-C_{18}$, preferably $C_{12}-C_{16}$, alkyl polyglycosides with average degrees of glycosidation ranging from about 1.1 to about 2.7, preferably from about 1.2 to about 2.5, are preferred.

Anionic nonsoap surfactants can be exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8-C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

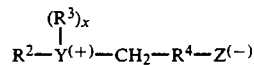

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-P-diethyl-P-3,6,9-trioxatetradexocylphosphonio]-2-hydroxypropane-1-phosphate; 3-N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl)ammonio]butane-1-carboxylate; 3-[S-ethyl-S-(3-dodecoxy-2-hydroxypropyl)sulfonio] -propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl bis-(2-hydroxyethyl) sulfopropyl betaine, amido betaines amidosulfobetaines, and the like.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

Many additional nonsoap surfactants are described in McCUTCHEON'S, DETERGENTS AND EMULSIFIERS, 1979 ANNUAL, published by Allured Publishing Corporation, which is incorporated here by reference.

The above-mentioned surfactants can be used in the cleansing bath/shower compositions of the present invention. The anionic surfactants, particularly the alkyl sulfates, the ethoxylated alkyl sulfates and mixtures thereof are preferred. More preferred are $C_{12}$–$C_{14}$ alkyl anionic surfactants selected from the group consisting of sodium alkyl glycerol ether sulfonate, sodium lauroyl sarcosinate, sodium alkyl sulfate, sodium ethoxy (3) alkyl sulfate, and mixtures thereof.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

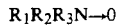

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

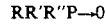

$$RR'R''P \rightarrow O$$

wherein R contains an alkyl, alkenyl or monohydroxyalkyl radical ranging from 8 to carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecyl methyl sulfoxide, 3-hydroxytridecyl methyl sulfoxide, 3-hydroxy-4-dodecoxybutyl methyl sulfoxide.

The pH of the cleansing bath/shower compositions herein is generally from about 7.5 to about 9.5, preferably from about 8 to about 9 as measured in a 10% aqueous solution at 25° C.

Assessment of Petrolatum Particle Size

Particle size distribution is measured in neat product under a microscope with a 10X phase contrast objective. The particle size distribution is counted manually. The frequency distribution of the petrolatum particle sizes is converted to a weight distribution by assuming that the petrolatum particles are uniform spheres. The "weight average particle size" is the average particle size based on the arithmetic average of the weight distribution. This standard method for calculating size averages is described in detail in *Handbook of Chemical Microscopy, Vol. 1, Third Ed.* by E. M. Chamot and C. W. Mason (Wiley: New York, 1958).

Quantitation of Petrolatum Deposition

Petrolatum deposition from products is measured by one of two protocols, both modeled after how products are typically used by consumers. One protocol is done "in vitro", while the second is done "in vivo".

In the in vitro protocol, a model skin substrate is used which is a collagen sheet that has a surface topography similar to human skin and has been pre-hydrated. Small pieces of the substrated are mounted over flask openings to secure them for exposure to lather. The lather is generated in the palms of hands under a controlled procedure (one gram of product plus 3 ml of water for 10 seconds). The mounted substrate is then exposed to the combined lather by overturning the flask and rubbing it on the palm of the hand. This lathering process is continued for 10 seconds and, after allowing the lather to remain on the substrate for 5 seconds, it is rinsed with warm tap water for 10 seconds. The exposed skin substrate is then cut from the mount and dried prior to analysis. The analysis procedure is to submerge the substrate in 1:1 ethanol:heptane and then analysis of this extract by standard gas chromatographic methods.

The in vivo protocol is similar to the in vitro one described above, except the lather generated in the palm of the hand is applied to the opposite forearm. The time that the lather remains on the forearm is 30 seconds (compared to the 5 seconds on the collagen substrate). The deposited petrolatum is then extracted by strapping an open-ended glass cylinder to the forearm and adding the ethanol/heptane solvent to this cylinder. As above, the extract is then analyzed according to standard gas chromatographic methods.

A Method for Making Cleansing Moisturizers

The method of manufacture of both the products of the present invention uses standard industry equipment and procedures.

Specifically, a general process for an 1800 grams size batch using a Tokoshu Kiko Agi Homo Mixer (Model 2M-2) mixer as outlined below. However, mixing times will vary with equipment, batch size, etc.

1. The oil phase containing the fatty acids, antimicrobial (if added), etc. is added to a sanitary, agitated and jacketed stainless steel vessel with side sweep mixing, homogenization and vacuum capabilities;.
2. The oil phase is heated to about 80° C.;
3. In a separate container, the water phase is prepared containing polymers, polyol liquids, synthetic surfactants and other water-soluble minors and heated to 80° C. with agitation;
4. After the oil phase reaches 80° C., a vacuum is applied (450 mmHg) and stirring (20 RPM) and homogenization (~5,000 RPM) are started;
5. The appropriate base for the in situ soap formation is added via the vacuum port and mixed for 5 minutes;
6. Next, the water phase is added via the vacuum port and mixed for 10 minutes;
7. The homogenizer is turned off and the product cooled to about 48° C. at which other minors such as aloe vera may be added;
8. Upon further cooling (to about 35° C.), the vacuum is broken and perfume is added;
9. The product may stand for about 1 day prior to adding materials such as petrolatum or these materials may be added immediately;
10. In the case of the product standing, the product is reheated to about 35° C., a small vacuum applied (650 mmHg) and the side sweep mixers (about 10 RPM) are started prior to petrolatum addition.
11. Petrolatum particle size is controlled by mix time and addition temperature. The shorter the mix time and the lower the temperature, the higher the proportion of larger particles.

EXAMPLES AND FORMULAS

The following examples and formulas are illustrative and are not intended to limit the scope of the invention(s). The preferred method of making the semi-solid compositions of the present invention is set out above. All levels, ranges, temperatures, results, etc., used herein are approximations, unless otherwise specified. All formula percentages are expressed as a weight percentage unless otherwise specified.

EXAMPLES 1-3

Examples 1-3 are identical cream (semi-solid) compositions but for petrolatum particle size. The effect of petrolatum particle size upon skin deposition is shown in Table 1. As can be seen, all products in these examples contain the same level of petrolatum (15%), but have different average particle sizes. Widely different levels of petrolatum deposition are observed, and a direct correlation to particle size is inferred. The compositions with the larger petrolatum particles, Examples 2 and 3, have petrolatum depositions superior to that of Experimental Example 1.

TABLE 1

| | Mixing Times | | |
|---|---|---|---|
| | Ex. 1 | Ex. 2 | Ex. 3 |
| Ingredients (Wt. %) | | | |
| Water | 43.60 | 43.60 | 43.60 |
| Stearic Acid | 2.81 | 2.81 | 2.81 |
| Palmitic Acid | 2.33 | 2.33 | 2.33 |
| Myristic Acid | 3.25 | 3.25 | 3.25 |
| Lauric Acid | 1.31 | 1.31 | 1.31 |
| Triclosan | 0.26 | 0.26 | 0.26 |
| In situ potassium soap | 14.45 | 14.45 | 14.45 |
| Glycerin | 12.75 | 12.75 | 12.75 |
| $Na_5$Pentetate | 0.09 | 0.09 | 0.09 |
| $Na_4$Etidronate | 0.09 | 0.09 | 0.09 |
| Sodium Lauroyl Sarcosinate | 3.40 | 3.40 | 3.40 |
| Polyquaternium-10 | 0.43 | 0.43 | 0.43 |
| Aloe Vera Gel | 0.01 | 0.01 | 0.01 |
| Fragrance | 0.26 | 0.26 | 0.26 |
| Petrolatum | 15.00 | 15.00 | 15.00 |
| | 100.00 | 100.00 | 100.00 |
| Characterization: | | | |
| Petrolatum Weight Average Particle Size (um) | 22.7 | 69.9 | 90.5 |
| Petrolatum Deposition in vitro (micrograms/$cm^2$) | 30 | 46 | 73 |
| Mixing Time (min.) at 10 RPMs | 30 | 20 | 5 |

The semi-solid compositions, Examples 1, 2, and 3 are mixed for 30, 20, and 5 minutes, respectively, at 10 RPMs and the Petrolatum Weight Average particle sizes are respectively about 22.7, 69.9, and 90.5 microns. The Petrolatum Depositions in vitro (Micrograms/$cm^2$) are 30, 46, and 73, respectively. The larger particles deposit more efficiently.

EXAMPLES 4-6

Preferred Compositions

Examples 4-6 (Table 2) are cream compositions that demonstrate that varying levels of petrolatum can be incorporated. From the deposition data, it is apparent that the particle size of the petrolatum is the stronger determinant of the level of deposited petrolatum, not the amount of petrolatum in the product.

TABLE 2

| | Example 4 | Example 5 | Example 6 |
|---|---|---|---|
| Ingredients: (Wt. %) | | | |
| Water | 50.51 | 49.75 | 48.21 |
| Stearic Acid | 3.25 | 3.20 | 3.10 |
| Palmitic Acid | 2.70 | 2.66 | 2.58 |
| Myristic Acid | 3.76 | 3.71 | 3.59 |
| Lauric Acid | 1.52 | 1.49 | 1.45 |
| Triclosan | 0.29 | 0.29 | 0.28 |
| In situ potassium soap | 16.74 | 16.49 | 15.98 |
| Glycerin | 14.77 | 14.55 | 14.10 |
| $Na_5$Pentetate | 0.10 | 0.10 | 14.10 |
| $Na_4$Etidronate | 0.10 | 0.10 | 0.09 |
| Sodium Lauroyl Sarcosinate | 3.94 | 3.88 | 3.76 |
| Polyquaternium-10 | 0.49 | 0.49 | 0.47 |
| Aloe Vera Gel | 0.01 | 0.01 | 0.01 |
| Fragrance | 0.29 | 0.29 | 0.28 |
| Petrolatum | 1.50 | 3.00 | 6.00 |
| | 100.00 | 100.00 | 100.00 |
| Characterization: | | | |
| Petrolatum Weight Average Particle Size (microns) | 73.6 | 76.7 | 79.3 |
| Petrolatum Particle Size Distribution (%) | | | |
| <20 microns | 37 | 51 | 48 |
| >20 microns | 63 | 49 | 52 |

TABLE 2-continued

| | Example 4 | Example 5 | Example 6 |
|---|---|---|---|
| Petrolatum Deposition in vivo (micrograms/$cm^2$) | 57 | 62 | 61 |
| Mixing Time (min.) at 10 RPMs | 5 | 5 | 5 |

Example 5, a highly preferred cleansing product, is packaged in a 200 gram plastic squeeze tube having an orifice of about 6 mm. The product is used by squeezing the tube.

The compositions set out in Table 3 are prepared using the above method—Steps 1-8.

TABLE 3

| Stable Creams | 7 | 8 | 9 |
|---|---|---|---|
| Ingredients: | | | |
| Water | 43.79 | 55.19 | 51.07 |
| Stearic Acid | 3.89 | 2.90 | 3.53 |
| Palmitic Acid | 3.21 | 2.39 | 2.91 |
| Myristic Acid | 4.49 | 3.35 | 4.07 |
| Lauric Acid | 1.81 | 1.35 | 1.64 |
| Triclosan | 0.30 | 0.30 | 0.30 |
| In situ potassium soap | 23.00 | 15.00 | 15.00 |
| $Na_5$Pentetate | — | — | 0.22 |
| $Na_4$Etidronate | — | — | 0.22 |
| Sodium Lauroyl Sarcosinate | 4.00 | 4.00 | 4.00 |
| Polyquaternium-10 | 0.50 | 0.50 | 0.50 |
| Aloe Vera Gel | 0.01 | 0.01 | 0.01 |
| Fragrance | — | — | 0.28 |

Petrolatum is added to these stable base creams at the levels shown in Table 4.

TABLE 4

| Examples: | 10 | 11 | 12 |
|---|---|---|---|
| Ingredients: | | | |
| Water | 43.13 | 54.36 | 50.30 |
| Stearic Acid | 3.83 | 2.87 | 3.48 |
| Palmitic Acid | 3.16 | 2.35 | 2.87 |
| Myristic Acid | 4.42 | 3.30 | 4.01 |
| Lauric Acid | 1.78 | 1.33 | 1.62 |
| Triclosan | 0.30 | 0.30 | 0.30 |
| In situ potassium soap | 22.66 | 14.78 | 14.78 |
| $Na_5$Pentetate | — | — | 0.22 |
| $Na_4$Etidronate | — | — | 0.22 |
| Sodium Lauroyl Sarcosinate | 3.94 | 3.94 | 3.94 |
| Polyquaternium-10 | 0.49 | 0.49 | 0.49 |
| Aloe Vera Gel | 0.01 | 0.01 | 0.01 |
| Fragrance | — | — | 0.28 |
| Petrolatum | 1.5 | 1.5 | 1.5 |

Petrolatum is added to the stable creams 7-9 (Table 3) Examples 10-12, to provide semi-solid cleansing cream. Examples 10-12 show varying ratios and levels of fatty acid and soap used for compositions of the present invention.

The semi-solid cleansing cream compositions, Examples 10, 11, and 12 are made by adding the petrolatum (Step 9) to each parent base composition (7-9) and mixing for about 5 minutes at 10 RPMs. The Petrolatum Weight Average particle sizes for Examples 10-12 are greater than about 50 microns. Examples 10-12 provide improved mildness and moisturization over the parent base cream compositions 7-9, as well as over comparable compositions with much smaller petrolatum particle sizes.

EXAMPLE 13

| Personal Cleansing Bar with Petrolatum | |
|---|---|
| Sodium Myristate | 20.00 |
| Water | 28.07 |
| Coco Betaine | 6.00 |
| Sodium Lauryl Sarcosinate | 8.00 |
| Stearyl Dimethyl Benzyl Ammonium Chloride (SDBAC) | 3.00 |
| Glycerine | 15.00 |
| Petrolatum | 15.00 |
| Perfume | 0.50 |
| Miscellaneous | 1.43 |
| NaCl (Sodium Chloride) | 3.00 |
| | 100.00 |

A two-kilogram batch of the above composition (Example 13) is made by the following steps:
1. Myristic acid is melted at −65° C. (150° F.).
2. In a separate vessel, sodium hydroxide, water, and NaCl are mixed at 77°-82° C. This mixture is added to the fatty acid of Step 1 to neutralize and form an in situ soap while mixing at low speed for about 7-10 minutes.
3. Add Coco Betaine and mix for 10 minutes on low speed.
4. Sodium Lauryl Sarcosinate is added and mixed for 10 minutes on low speed.
5. Glycerine is added and mixed for 3 minutes on low speed.
6. SDBAC is added and mixed for 2 minutes on low speed.
7. Petrolatum is added and mixed for 2 minutes on low speed. The temperature is maintained at −82° C. (180° F.) for Steps 3-7.
8. The composition is poured into molds, cooled, then removed from the molds.

A hard bar is obtained. The petrolatum particle size for the bar is determined by wetting and lathering the bar, and transferring a droplet off the wet bar onto a slide. A coverslip is placed on the droplet and the slide is examined under an optical light microscope, using a 40× objective. Several photographs are taken (total magnification=325×) and the particle size distribution is counted manually. The petrolatum in the lather for Example 13 has a particle size distribution of −25% of the particles, having a particle size of 10 micron or greater.

This bar, like the semi-solid creams of Examples 2-6 and 10-12 with said large petrolatum particles, provide both mild cleansing and improved moisturization of the skin over comparable compositions without petrolatum as well as comparable compositions with smaller petrolatum particles.

The compositions of the present invention, particularly the semi-solid, has improved mildness over comparable compositions without petrolatum.

What is claimed is:

1. A stable dispersoidal semi-solid soap cleansing and moisturizing composition, by weight, consisting essentially of:
   (A) from about 7% to about 33% potassium $C_8$–$C_{22}$ fatty acid soap;
   (B) from about 4% to about 18% $C_8$–$C_{22}$ free fatty acid;
   (C) from about 40% to about 70% water;
   (D) from about 5% to about 30% of a polyol selected from the group consisting of: glycerol (glycerin), propylene glycol, polypropylene glycols, polyethylene glycols, ethyl hexanediol, hexylene glycols, and mixtures thereof; and
   (E) from about 0.5% to about 15% petrolatum having a particle size distribution in which 20% to 80% of the particles are from 10 to 120 microns;
   wherein said semi-solid has a viscosity of from about 60,000 cps to about 400,000 cps at 25° C.

2. A semi-solid composition of claim 1 wherein said fatty acid of said (A) and (B) has an Iodine Value of from zero to about 15; and wherein said soap and said free fatty acid have a weight ratio of about 1.3:1 to about 1.8:1.

3. A semi-solid composition of claim 2 wherein said composition contains from about 0.7% to about 13% of said petrolatum with a weight average particle size of from 50 microns to 110 microns; and wherein said Iodine Value is less than 10 and wherein said semi-solid has a viscosity of 70,000 cps to about 200,000 cps.

4. A semi-solid composition of claim 2 wherein said composition contains petrolatum at a level of about 1% to about 6% and said petrolatum has a melting point of from about 50° to about 60° C.; and wherein said fatty acid Iodine Value is less than 3.

5. A semi-solid composition according to claim 1 wherein said composition contains from about 1% to about 10% of a high lathering synthetic surfactant.

6. A semi-solid composition according to claim 1 wherein said (A) and (B) has a ratio of from about 1.35:1 to about 1.7:1; and wherein said fatty acid is highly saturated and has an Iodine Value of from zero to about 10; and wherein said fatty acid is composed of alkyl chain lengths ranging from $C_{10}$ to $C_{20}$; and wherein said composition contains from about 2.5% to about 6.5% of a higher lathering synthetic surfactant.

7. A semi-solid composition according to claim 1 wherein said composition, component (D), contains from about 10% to about 25% glycerol.

8. A semi-solid composition according to claim 6 wherein said fatty acid has an Iodine Value of from zero to 3 and wherein said synthetic surfactant is lauroyl sarcosinate with cations selected from the group consisting of sodium or potassium, and mixtures thereof.

9. A semi-solid composition according to claim 8 wherein said composition contains from about 0.15 to about 5% cationic polymer selected from the group consisting of:
   (I) cationic polysaccharides
   (II) cationic copolymers having monomers selected from saccharides and synthetic monomers,
   (III) synthetic polymers selected from the group consisting of:
      (A) cationic polyalkylene imines,
      (B) cationic ethoxypolyalkylene imines, and
      (C) cationic poly(N-(3-(dimethylammonio)-propyl(N'-(3-ethyleneoxyethylene dimethylammonio)propyl)urea dichloride); and
   (IV) cationic protein derivatives.

10. A semi-solid composition according to claim 9 wherein the cationic polymer level is from about 0.3% to about 3%.

11. A semi-solid composition according to claim 1 wherein said composition also contains from about 0.5% to about 10% of an emollient selected from the group consisting of esters of fatty acids; mineral oil; silicone oils and gums; glycerin mono-, di-, and triesters; epidermal and sebaceous hydrocarbons; lanolin and derivatives, and mixtures thereof.

12. A stable semi-solid composition according to claim 1 wherein said composition is made by the following steps:
1. heating and mixing said free fatty acid to provide a stable melt;
2. forming an aqueous potassium dispersion of soap and free fatty acid having a ratio of about 1.3:1 to about 1.8:1;
3. adding said water, polyol and optionally up to 10% of a mild, lathering surfactant to said dispersion with mixing;
4. cooling the dispersion of Step 3 to a temperature below the melting point of said petrolatum.
5. adding said petrolatum with controlled mixing to provide said dispersoidal semi-solid personal cleansing composition.

13. A semi-solid composition according to claim 12 comprising said potassium soap made in situ with potassium hydroxide.

14. The stable semi-solid composition of claim 12 wherein said soap and said free fatty acid of Step 2 are heated to a temperature of from about 75° C. to about 90° C.

15. The semi-solid composition of claim 12 wherein said method includes deaeration of said semi-solid of Step 5.

16. The semi-solid composition of claim 12 wherein said cooling is conducted at a rate of about 0.5° C. per minute or slower.

17. A stable cleansing bar composition, by weight, comprising;
(A) from about 5% to about 75% of a substantially saturated fatty acid material selected from the group consisting of $C_8-C_{22}$ free fatty acid and fatty soap and mixtures thereof;
(B) from about 10% to about 90% water; and
(C) from about 0.5% to about 35% petrolatum having a particle size distribution wherein from about 20% to about 80% of said particles have a particle size of from 10 microns to about 110 microns.

18. A stable dispersoidal semi-solid soap cleansing and moisturizing composition, by weight, comprising:
(A) from about 7% to about 33% by weight of potassium $C_8-C_{22}$ fatty acid soap;
(B) from about 4% to about 18% $C_8-C_{22}$ free fatty acid;
(C) from about 40% to about 70% water;
(D) from about 5% to about 30% of a polyol selected from the group consisting of: glycerol (glycerin), propylene glycol, polypropylene glycols, polyethylene glycols, ethyl hexanediol, hexylene glycols, and mixtures thereof;
(E) from about 0.5% to about 15% of a lipophilic emollient selected from the group consisting of: petrolatum; mineral oil; esters of fatty acids, glycerin mono-, di-, and tri-esters; epidermal and sebaceous hydrocarbons, silicone oils and gums; lanolin and derivatives, and mixtures thereof; and
wherein from about 20% to about 80% of said emollient has a particle size distribution of from about 10 microns to about 110 microns; and wherein said semi-solid has a viscosity of from about 60,000 cps to about 400,000 cps at 25° C.

19. The composition of claim 18 wherein said emollient is selected from the group consisting of petrolatum and esters of fatty acids wherein said fatty acid esters are of structure $$R_1-C(=O)-OR_2$$

and wherein
$R_1, R_2 = C_8-C_{22}$, ricinoleate, 12-hydroxy stearic and wherein $R_1$ and/or $R_2$ alkyl chain can be saturated or unsaturated.

20. The composition of claim 19 wherein said emollient is petrolatum.

21. The composition of claim 18 wherein from about 25% to about 80% of said emollient has a particle size of from about 30 micron to about 110 micron.

22. The composition of claim 21 wherein from about 25% to about 80% of said emollient particles have a particle size of from about 60 micron to about 100 micron.

23. A stable dispersoidal semi-solid soap cleansing and moisturizing composition, by weight, comprising:
(A) from about 7% to about 33% potassium $C_8-C_{22}$ fatty acid soap;
(B) from about 4% to about 18% $C_8-C_{22}$ free fatty acid;
(C) from about 40% to about 70% water;
(D) from about 5% to about 30% of a polyol selected from the group consisting of: glycerol (glycerin), propylene glycol, polypropylene glycols, polyethylene glycols, ethyl hexanediol, hexylene glycols, and mixtures thereof; and
(E) from about 0.5% to about 15% petrolatum having a particle size distribution in which from 20% to 80% of the particles are from 10 microns to about 110 microns;
wherein said semi-solid has a viscosity of from about 60,000 cps to about 400,000 cps at 25° C.; and wherein said petrolatum is added to a stable cream comprising said (A)-(D) at a temperature below said petrolatum's melting point.

24. A semi-solid composition of claim 23 wherein said level of petrolatum is from 0.5% to about 6%; and wherein said fatty acid of said (A) and (B) has an Iodine Value of from zero to about 15; and wherein said soap and said free fatty acid have a weight ratio of about 1.3:1 to about 1.8:1.

25. A semi-solid composition of claim 24 wherein said petrolatum has a weight average particle size of from 45 microns to 120 microns; and wherein said Iodine Value is less than 10 and wherein said semi-solid has a viscosity of 70,000 cps to about 200,000 cps.

26. A semi-solid composition of claim 24 wherein said composition contains petrolatum at a level of about 1% to about 6% and said petrolatum has a melting point of from about 50° to about 60° C.; and wherein said fatty acid Iodine Value is less than 3.

27. A semi-solid composition according to claim 23 wherein said composition contains from about 1% to about 10% of a high lathering synthetic surfactant.

28. A semi-solid composition according to claim 23 wherein said (A) and (B) has a ratio of from about 1.35:1 to about 1.7:1; and wherein said fatty acid is highly saturated and has an Iodine Value of from zero to about 10; and wherein said fatty acid is composed of alkyl chain lengths ranging from $C_{10}$ to $C_{20}$; and wherein said composition contains from about 2.5% to about 6.5% of a higher lathering synthetic surfactant.

29. A semi-solid composition according to claim 23 wherein said composition contains from about 10% to about 25% of said polyol and said polyol is glycerol.

30. A semi-solid composition according to claim 28 wherein said fatty acid has an Iodine Value of from zero to 3 and wherein said synthetic surfactant is lauroyl sarcosinate with cations selected from sodium or potassium, and mixtures thereof.

31. A semi-solid composition according to claim 30 wherein said composition contains from about 0.15 to about 5% cationic polymer selected from the group consisting of:

(I) cationic polysaccharides (II) cationic copolymers having monomers selected from saccharides and synthetic monomers, (III) synthetic polymers selected from the group consisting of:

(A) cationic polyalkylene imines, (B) cationic ethoxypolyalkylene imines, and (C) cationic poly(N-(3-(dimethylammonio)-propyl(N'-(3-ethyleneoxyethylene dimethylammonio)propyl)urea dichloride); and (IV) cationic protein derivatives.

32. A semi-solid composition according to claim 31 wherein the cationic polymer level is from about 0.3% to about 3%.

33. A semi-solid composition according to claim 23 wherein said composition also contains from about 0.5% to about 10% of an emollient selected from the group consisting of esters of fatty acids; mineral oil; silicone oils and gums; glycerin mono-, di-, and tri-esters; epidermal and sebaceous hydrocarbons; lanolin and derivatives, and mixtures thereof.

34. A semi-solid composition according to claim 33 comprising said potassium soap made in situ with potassium hydroxide.

* * * * *